United States Patent [19]

Rudin

[11] 4,315,146
[45] Feb. 9, 1982

[54] PROCESS AND APPARATUS FOR SCATTER REDUCTION IN RADIOGRAPHY

[75] Inventor: Stephen Rudin, Williamsville, N.Y.

[73] Assignee: The Research Foundation of State University of New York, Albany, N.Y.

[21] Appl. No.: 169,887

[22] Filed: Jul. 17, 1980

Related U.S. Application Data

[63] Continuation of Ser. No. 67,282, Aug. 17, 1979, abandoned.

[51] Int. Cl.$^3$ ............................................. G01N 23/00
[52] U.S. Cl. .................................. 250/515; 250/514; 250/509; 250/445 T
[58] Field of Search ............... 250/514, 515, 508, 509, 250/505, 503, 445 T

[56] References Cited

U.S. PATENT DOCUMENTS

| | | | |
|---|---|---|---|
| 2,806,147 | 9/1957 | Stellmacher et al. | 252/514 |
| 2,825,817 | 3/1958 | North | 252/514 |
| 3,866,047 | 2/1975 | Hounsfield | 252/514 |

FOREIGN PATENT DOCUMENTS

521746  3/1921  France .

Primary Examiner—Bruce C. Anderson
Attorney, Agent, or Firm—Michael L. Dunn

[57] ABSTRACT

A process and apparatus for reducing detected radiation scatter in radiography. The process comprises interposing synchronized rotating radiation shields between the object being radiographed and the detector and desirably between the radiation source and the object. Openings in the shields are aligned in such a way as to permit primary radiation to pass to the detector while stopping most radiation scatter. The apparatus comprises the shields with openings, means for mounting the shields and means for rotating the shields at appropriate speeds.

36 Claims, 4 Drawing Figures

PROCESS AND APPARATUS FOR SCATTER REDUCTION IN RADIOGRAPHY

This is a continuation, of application Ser. No. 067,282, filed Aug. 17, 1979 abandoned.

The invention described herein was made in the course of work under a grant or award from the Department of Health, Education and Welfare.

BACKGROUND OF THE INVENTION (a) Field of the Invention

This invention relates to diagnostic radiology and in particular relates to the use of high energy radiation to form images of internal structures upon a sensing means such as x-ray film. The invention more particularly relates to a method and apparatus for reducing detection of radiation scatter in forming such images.

(b) History of the Prior Art

Originally, x-ray photographs were taken simply by directing x-rays from a source, e.g., an original rontgen ray tube, through an object such as an anatomical structure to a detector such as an x-ray film. This historical arrangement did not include additional devices to reduce hazards to a patient or to enhance the quality of the detected x-ray image.

Later x-ray devices not only provided improved x-ray tubes such as tubes which could independently control intensity and wave length of x-rays but also incorporated filters for eliminating radiation outside of the useful x-ray range and included means for enhancing the contrast of the image by eliminating at least a portion of radiation scatter from the object such as a patient to the detector. Such scatter often results when high energy radiation interacts with molecular fields or particles. Scattered radiation is usually emitted in a direction different than the direction of the incoming primary radiation. The scattered radiation thus causes exposure of the detector to radiation at all locations thus reducing contrast of the detected image with the background.

The most usual method for reducing scatter historically has been and remains radiographic grids which consist of a series of lead foil strips separated by x-ray partially transparent spacers. The lead foil acts to intercept secondary or scattered radiation which approaches the detector at an inappropriate angle. Such grids have, however, certain undesirable characteristics. For example, contrast is still not as high as desired since all scatter is still not eliminated, primaries are absorbed by interspaces and grid lines become apparent on the x-ray image since the lead strips absorb primary radiation from the radiation source.

Attempts have been made to eliminate the appearance of the grid pattern in the x-ray image by moving the grid in a direction essentially perpendicular to radiation passing from the source to the detector; however, such a moving grid did nothing to increase contrast. There has also been an attempt to utilize linearly moving aligned slit devices to increase contrast. The devices have to be moved at a uniform speed and have to reach that speed before the x-ray is taken. This requires that the x-ray be taken in a precisely timed relationship to slit motion. Furthermore, vibration within the system cannot be tolerated and absolutely uniform x-ray output must be maintained during exposure to prevent unwanted patterns on the detector. Currently and perhaps subsequent to the present invention, an attempt is being made to increase contrast by mounting two slitted discs on a single axis and rotating the discs about the single axis while directing x-rays from the axis through the first slitted disc to the object or patient through the second slitted disc and a grid to the detector. This device has not proven desirable since a patient or object and detector, in order to be placed in a perpendicular relationship to incoming radiation, must of necessity be at an angle to the rotating discs. Such arrangement permits very little flexibility with respect to the location of the patient in relationship to the x-ray source and the rotating discs and contrast is not as good as is desirable. Furthermore, due to the use of the grid, grid lines are still present.

BRIEF DESCRIPTION OF THE INVENTION

In accordance with the present invention, there is provided a process and apparatus which eliminates all grid lines and simultaneously dramatically enhances image contrast yet permits adjustments of the object or patient with respect to the source and the detector which therefore permits acceptable images to be formed with lower radiation doses thus permitting reduction in patient exposure.

The apparatus, in accordance with the invention, for reducing detection of radiation scatter from an object through which high energy radiation passes within a flux pyramid from a source to a radiation detection means comprises a series of at least two radiation shields, each of which has front and rear surfaces which are large relative to the thickness of the shield. The apparatus further comprises means for rotatably mounting the shields in a spatially separated relationship with each other between the object and the detection means so that each of the shields covers an entire section of the flux pyramid and so that each of the shields is rotatable about its own central axis through its center of gravity.

For conventional radiography, the shields are mounted so that the front surface of each shield faces toward the source and the rear surface of each shield faces away from the source. The surfaces are approximately parallel to the plane of the detector. The apparatus further comprises a means for rotating each of the shields at its own angular velocity at a constant angular velocity ratio. The rate of rotation of each shield is preferably constant and most preferably the same as the angular velocities of the remaining shields.

Each of the shields is further provided with a series of openings smaller than the object. The openings pass through the shield from the front to the rear surfaces and allow radiation to pass through the shield from the source to the detection means. Each of the shields is provided with the openings in shapes and positions such that at least a portion of the radiation in a straight line from a uniform source toward the detection means passes through openings in all of the shields to strike the detection means in essentially uniform coverage of the detection means when the object is absent and when each of the shields is in rotation about its central axis at its own angular velocity at a constant angular velocity ratio. "Essentially uniform coverage" means uniform coverage ±10% between square millimeter areas on the detector not considering the effects of different distances of each of such areas from the uniform source.

Desirably, the apparatus further comprises an additional shield similar to the other shields which is rotatably mounted between the source and the object in a spatially separated related relationship with the other shields so that the additional shield also covers an entire section of the flux pyramid and is also rotatable about its own central axis through its center of gravity. The additional shield is also mounted so that its front surface faces toward the source and the rear surface faces away from the source and so that the surfaces, when planar and parallel, are approximately parallel to the plane of the detector. Means is provided for rotating each of the shields including the additional shield at its own angular velocity at a constant angular velocity ratio. The angular velocity of the additional shield is desirably constant and preferably the same as the velocities of the remaining shields when the opening shapes and patterns on the shields are proportionally the same. The additional shield is also provided with a series of openings passing through the shield from the front to the rear surface which allow radiation to pass through the shield from the source to the detection means. The additional shield is provided with the openings in shapes and positions such that at least a portion of radiation in a straight line from a uniform source toward the detection means passes through openings in all of the shields to strike the detection means in essentially uniform coverage of the detection means when the object is absent and when each of the shields is in rotation about its central axis at its own angular velocity at a constant angular velocity ratio.

The process for reducing detection of radiation scatter from an object by a radiation detector which receives high energy radiation within a flux pyramid through the object from a radiation source comprises interposing a series of at least two spatially separated radiation shields between the object and a utilized surface of the detector such that each of the shields covers an entire section of the flux pyramid. Each of the shields have front and rear surfaces, which are large relative to the thickness of the shield. The surfaces are approximately parallel to the plane of the detector. The front surface of each shield faces the radiation source, i.e., within a 50 degree deviation from being normal to a line from the center of the source to the center of detector. Each shield has a central axis passing through its center of gravity in a direction substantially perpendicular to the front surface and each shield is provided with openings smaller than the object passing through the shield from the front to the rear surface. The ratio of the sum of the widths of the openings to the sum of the widths of solid shield areas on each shield is usually constant as such widths are measured along the arc of any circle having its center at the central axis of the shield and passing through the flux pyramid.

The process further comprises aligning the shields so that at least a portion of radiation in a straight line from the source toward the detector within the flux pyramid passes through openings in each of the shields to strike the detector. The process also comprises rotating each of said shields about its central axis at its own angular velocity to permit at least a portion of radiation in a straight line from a uniform source toward the detector within the flux pyramid to pass through openings in all of the shields to strike the detector in essentially uniform coverage of the utilized detector surface when the object is absent. Essentially uniform coverage is as previously defined.

Desirably, the process further comprises interposing an additional radiation shield between the source and the object such that the additional shield covers an entire section of the flux pyramid. The additional shield also has front and rear surfaces approximately parallel to the plane of the detector when the surfaces are planar and parallel and a central axis and openings as previously described. In all cases, the central axis of all shields are approximately perpendicular to the detector plane, i.e., the plane containing the detector surface. Approximately perpendicular may be perpendicular or within 10 and preferably within 5 degrees of perpendicular. Most desirably, the central axes are within 1 degree of perpendicular to the detector plane. When the additional radiation shield is utilized, the process also includes aligning all of the shields so that at least a portion of radiation in a straight line from the source toward the detector within the flux pyramid passes through openings in each of the shields to strike the detector. The process utilizing the additional shield further comprises rotating each of the shields about its central axis at its own angular velocity at a constant angular velocity ratio to permit at least a portion of radiation in a straight line from a uniform source toward the detector within the flux pyramid to pass through openings in all of the shields to strike the detector in essentially uniform coverage of the utilized detector surface when the object is absent. In both the apparatus and the process of the invention, the center of gravity of the shields preferably lie along the same straight line from the source.

DETAILED DESCRIPTION OF THE INVENTION

The present invention is an apparatus and process for reducing detection of radiation scatter from an object through which high energy radiation passes within a flux pyramid from a source to a radiation detector or detection means.

"High energy radiation", as used herein, means radiations having energies of from about 2 kiloelectron volts to about 2 megaelectron volts at wave lengths of from about 6.2 to about 0.0062 angstrom units. The radiation for medical diagnosis preferably has an energy of from about 10 to about 100 kiloelectron volts at wave lengths of from about 1.24 to about 0.124 angstrom units. In general, such radiation is x-ray radiation produced by an x-ray tube; however, the radiation may also be emitted from specially selected radioactive substances.

"Detector" or "detection means", may be considered equivalent and refer to any means for receiving radiation containing image information from an object in such a way that the received radiation is or can be converted into a visual display in photographic or video form. Video form means an image produced upon the phosphorescent or luminescent surface of a cathoderay tube, an image produced in liquid crystal or an image produced by light emitting diodes or the equivalent.

"Radiation scatter", as used herein, means deflected or secondary radiation resulting from the interaction of primary radiation with molecular or atomic forces or atomic particles within an object.

"Flux pyramid", as used herein, means the pyramid formed by radiation passing in a straight line from a radiation source such as an x-ray tube or a radioactive isotope to the utilized surface of the detector or detection means. The utilized surface of the detector or detection means is the actual surface intended to receive radiation containing image information. The utilized surface may be smaller than the entire surface of the detector since at any given time, there may not be a desire to utilize the entire detector surface to receive an image. The flux pyramid may be a pyramid comprising planar sides, may be a cone or may have curvilinear sides.

"Uniform source", as used herein, means a uniform point source of radiation which is constant over the time period of exposure, which time period is the time it takes for all of the shields to make an integral number of revolutions.

"Constant angular velocity ratio" means that the ratio of the angular velocities of any two shields is constant but is not necessarily the same as the ratio of the angular velocities of any other two shields.

The process in accordance with the invention comprises interposing a series of at least two spacially separated radiation shields between the object and the utilized surface of the detector. Each of the shields covers an entire section of the flux pyramid. For conventional radiography and usually for tomography, the section which is covered is a section of the pyramid formed by the intersection of a plane with the pyramid which plane is essentially parallel to the utilized surface of the detector. In general, the radiation shields are in parallel planes although a deviation of up to about 10° but preferably less than 5° from the parallel position, (i.e., approximately parallel) with the utilized surface (plane) of the detector can be tolerated.

Each of the shields have a front surface and a rear surface which are large relative to the thickness of the shield. The front surface of each shield faces the radiation source and the rear surface of each shield faces the utilized surface of the detector. The shields are manufactured of a material, such as lead, which will not permit the passage of radiation from the object to the detector surface.

Each shield is provided with a central axis which passes through its center of gravity in a direction substantially perpendicular to the front surface and to the intersected section of the flux pyramid. Each shield is provided with openings smaller than the object passing through the shield from the front to the rear surface. The ratio of the sum of the widths of the openings to the sum of the widths of solid shield areas is constant as such widths are measured along the arc of any circle having its center at the central axis of the shield and which circle passes through the flux pyramid. The openings in the shields are desirably in proportionally the same shapes and are disposed in proportionally the same patterns as in the remaining shields. The shapes of the openings are preferably circular sectors or trapezoids bounded by radii eminating from the central axis on two sides and by either straight parallel lines or arcs of circles having their centers at the central axis of the shields on the remaining two sides. The openings may also be of any other shape provided that the ratio of the sum of the widths of the openings to the sum of the width of the solid shield areas is constant along any arc of a circle having its center at the center of the shield as previously discussed.

The process further comprises aligning the shields so that at least a portion of radiation in a straight line from the source toward the detector within the flux pyramid passes through openings in each of the shields to strike the detector, and rotating each of the shields about its central axis at a constant angular velocity ratio to permit at least a portion of radiation in a straight line from the source toward the detector within the flux pyramid to pass through openings in all of the shields to strike the detector in essentially uniform coverage of the utilized detector surface when the object is absent. While each shield is rotated at its own angular velocity at a constant angular velocity ratio, it is obvious that the velocity ratio must be chosen to maintain alignment of the openings in the shields so that radiation can pass through the shield series to strike the detector. Furthermore, the angular velocities and ratios should be chosen so that radiation from the source actually uniformly scans the utilized detector surface through one or more sets of aligned openings in the shields.

In the process, it is desirable that an additional radiation shield be interposed between the source and the object such that the additional shield covers an entire section of the flux pyramid. The additional shield is of essentially the same construction as the previously described shield series, ie., the shield has front and rear surfaces, a central axis and openings.

The additional shield is aligned with the previously described shields so that at least a portion of radiation in a straight line from the source toward the detector within the flux pyramid passes through the openings in each of the shields to strike the detector. The additional shield is also rotated about its central axis at its own angular velocity at a constant angular velocity ratio again to permit at least a portion of radiation in a straight line from a uniform source toward the detector within the flux pyramid to pass through openings in all of the shields to strike the detector in essentially uniform coverage of the utilized detector surface when the object is absent. Interposing the additional shield between the source and the object reduces exposure of a patient to radiation which would not reach the detector surface because it is trapped by the series of shields between the patient and the detector surface. The additional shield only permits radiation which would pass through the series of shields between the patient and the detector to initially enter the patient. In addition, the additional shield reduces scatter by eliminating a substantial quantity of radiation which would strike the patient to cause increased scattering.

The apparatus in accordance with the invention, as previously discussed, comprises a series of at least two radiation shields, means for rotatably mounting each of the shields at its center of gravity and means for rotating each of the shields at its own angular velocity at a constant angular velocity ratio as previously discussed. The means for rotatably mounting the shields can be any suitable means but generally comprises a shaft to which the shield is perpendicularly mounted which shaft is supported by a suitable bearing such as a sleeve, roller or ball bearing. The bearings are in turn supported in a spatially separated relationship with each other by means of a suitable frame. Each of the shields are most desirably mounted on a single straight line passing from the source through the centers of gravity of the shields. The straight line is preferably not perpendicular to the shield surfaces for conventional radiography thus permitting radiation to pass almost perpendicularly through the shields and the straight line is usually, but not essentially, outside of the flux pyramid.

The means for rotating each of the shields at its own angular velocity at a constant angular velocity ratio and preferably at constant angular velocities is again any suitable means for accomplishing such rotation. Examples of such means include a synchronous motor for each of the shields to which each shield is directly or indirectly connected which rotates each shield at a speed to provide a constant angular velocity ratio or positive belt or chain drives, each connected to a constant speed shaft driven by a single motor or a series of gears connecting each of the shields to a single constant speed shaft.

The apparatus of the invention and its use in the process of the invention can be more particularly and clearly described by reference to the drawings.

Figure 1:
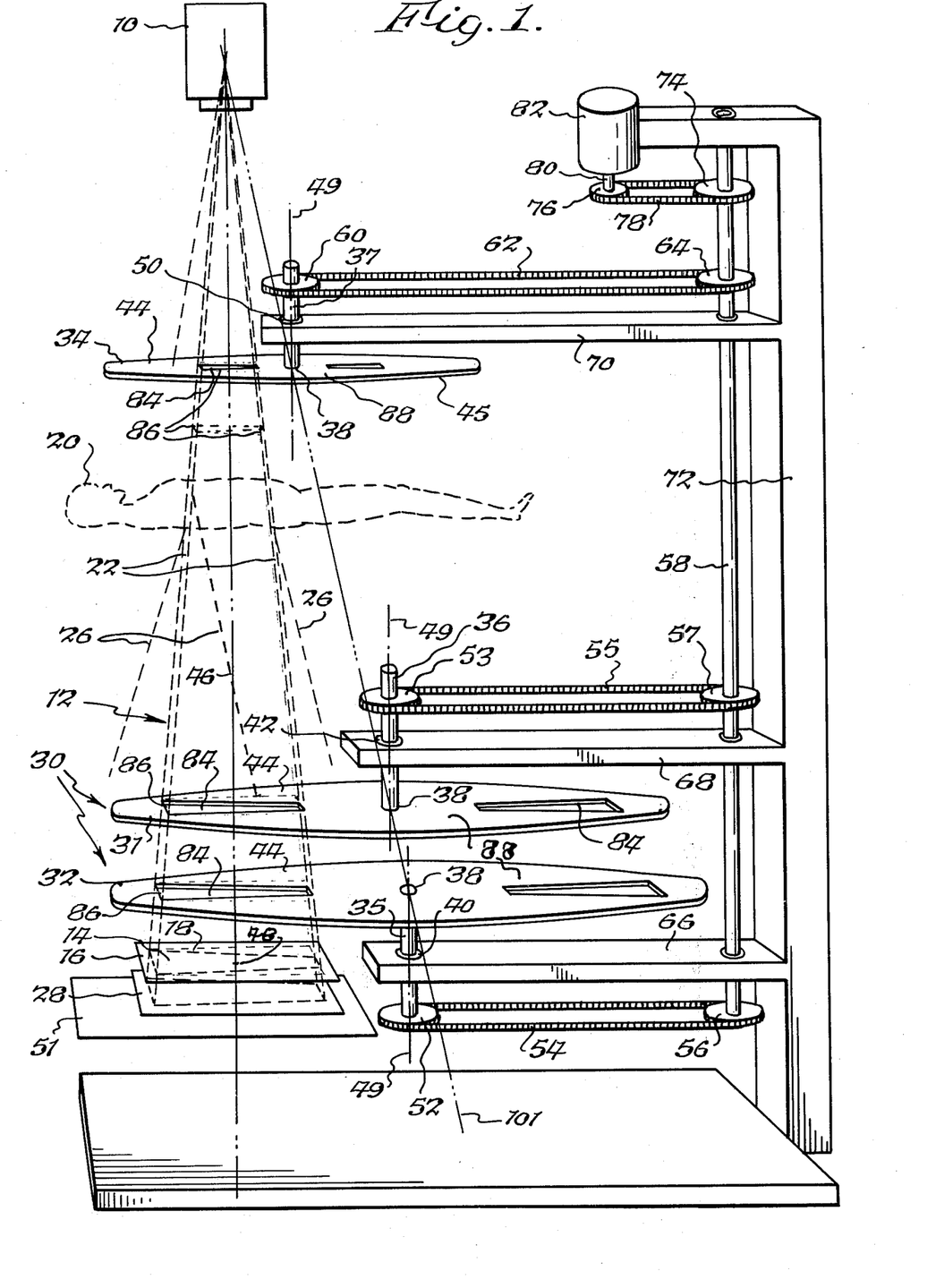
FIG. 1 is a side perspective view of an embodiment of the apparatus of the invention.

FIG. 1 is a perspective view of an apparatus in accordance with the preferred embodiment of the invention. FIG. 1 also illustrates the application of the process.

As can be seen in FIG. 1, radiation from a source 10 which is generally an x-ray tube, passes in a pyramid shape 12 to the utilized surface 14 of detector 16. Detector 16 is usually a luminescent screen. Pyramid 12 is defined by radiation passing from source 10 to the perimeter 18 of utilized surface 14. Radiation from source 10 passes through an object 20, usually in the form of a medical patient, having structures varying in density. The more dense portions of object 20 absorbs a relatively larger amount of radiation 22. Radiation 22 which has passed through object 20 therefore contains image information which is received by detector 16. A portion of radiation 22 may interact with molecular forces or particles within object 20 thus causing radiation scatter 26. When detector 16 is a luminescent screen, the image formed on the screen is either viewed directly, enhanced by amplification or photographed by means of photographic film 28 as shown in FIG. 1.

The apparatus, in accordance with the invention comprises a series 30 of radiation shields 31 and 32 interposed between object 20 and detector 16. The apparatus also desirably includes an additional shield 34 interposed between source 10 and object 20. Each of the shields is mounted by means of its own shield shaft 35, 36 and 37 so that each of the shields can be rotated about its center of gravity 38. Shields 31 and 32 are mounted in a spatially separated relationship by any suitable means and may be mounted separately in such a relationship. As shown in FIG. 1, shields 31 and 32 are mounted on shafts 36 and 35 respectively. Shafts 35 and 36 are rotatably mounted through bearings 40 and 42 so that shields 31 and 32 are free to rotate about their centers of gravity 38 and about central axes 49 which pass through the center of gravity 38 and in accordance with any embodiment of the present invention are approximately perpendicular to detector plane 51 containing the surface of detector 16. The shields are desirably mounted in a direction such that the upper surface 44 desirably faces radiation source 10 and is perpendicular to a line 46 from the center of radiation source 10 to the center 48 of utilized detector surface 14. Additional shield 34 is similarly mounted on an additional shield shaft 37 through bearing 50. Shafts 35 and 36 are provided with shaft sprockets 52 and 53 which are connected by means of chains 54 and 55 to drive shaft sprockets 56 and 57 which are mounted on drive shaft 58.

Similarly, additional shield shaft 37 is provided with a sprocket 60 connected by means of chain 62 to drive shaft sprocket 64. Bearings 40, 42 and 50 are supported by means of arms 66, 68 and 70 respectively. Arms 66, 68 and 70 are connected to frame upright 72. Drive shaft 58 is provided with drive sprocket 74 which is connected to motor sprocket 76 by means of drive chain 78. Motor sprocket 76 is connected to a shaft 80 of motor 82. Each of the shields 31 and 32 and additional shield 34 is provided with openings 84 which are preferably in the shape of truncated circular sectors. Openings 84 in each of shields 31, 32 and 34 are aligned in such a way that at least some of the radiation passing from source 10 to detector 16 can pass through openings 84 while most of radiation from source 10 which is scattered radiation, such as radiation 26, is absorbed by shields 31 and 32 and does not reach detector 16.

Desirably, each of shields 31 and 32 and 34 have openings 84 in proportionally the same locations and each of the shields 31, 32 and 34 completely intersect a section 86 of radiation pyramid 12. When it is said that openings 84 are in proportionally the same locations in shields 31, 32 and 34, it is meant that at any given time openings 84 constitute proportionally the same area in the pyramid sections 86 intersected by the respective shields and are in proportionally the same shapes and in proportionally the same locations within such sections. When this is the case, shields 31, 32 and 34 rotate at the same angular velocity about their respective centers of gravity 38.

In general, the shields, e.g., 31, 32 and 34, each individually have a constant ratio R for any circle passing through the flux pyramid.

$$R = \Sigma WO/SA$$

where $\Sigma WO$ is the sum of the widths of the openings around the circle and $\Sigma SA$ is the sum of the widths of the solid shield areas around the circle as all of such widths are measured on the arc of the circle. The R for any shield is desirably equal to or greater than the R for any shield which is between the source and the object, e.g., shield 34 and is desirably equal to or greater than the R for any shield closer to the source.

Figure 3:
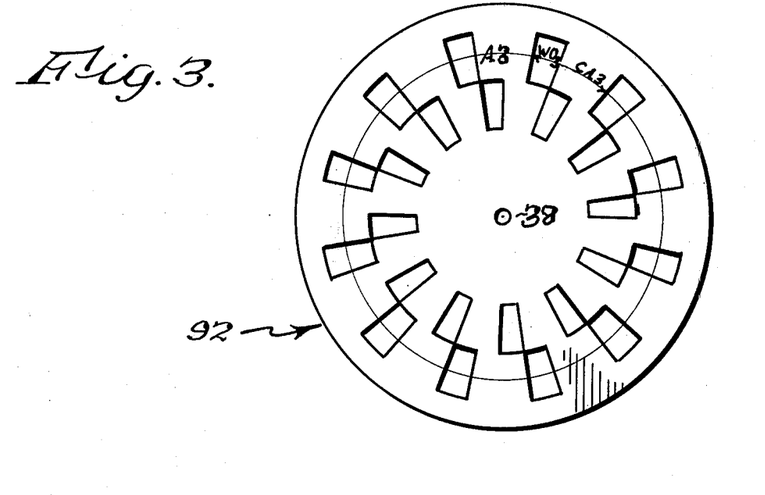
FIG. 3 is a top view of an embodiment of a rotatable shield in accordance with the invention.
Figure 4:
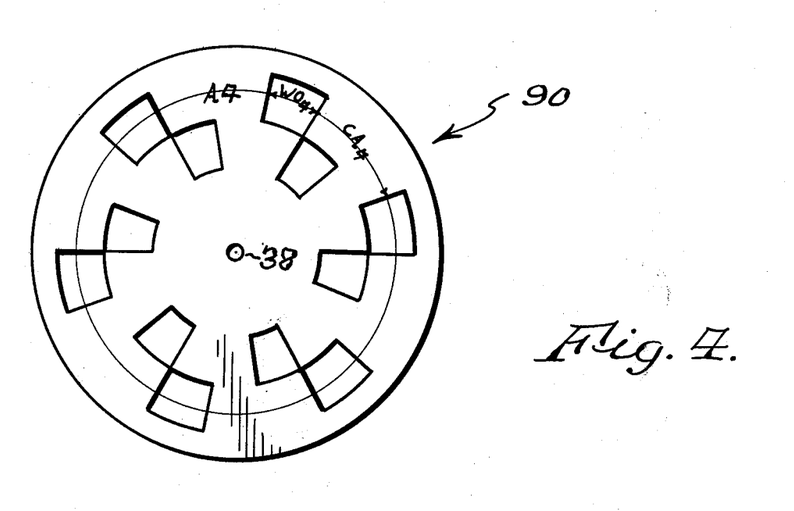
FIG. 4 is a top view of another embodiment of a rotatable shield in accordance with the invention.

It is possible for openings 84 through respective shields 31, 32 and 34 to occupy proportionally different areas within pyramid sections 86; however, when this is the case, as shown in FIGS. 3 and 4, the shields having fewer openings with the largest widths are rotated at a higher speed than the shields having more openings with proportionally smaller widths as measured along the arcs. The relative speed of the wheels is the same as the relative proportions of opening widths to total arc circumference. For example, the relative speeds of shields 90 and 92 at approximately the same pyramid section within the radiation pyramid would be the same as the ratio of $WO_3$, the width of the opening of the shield shown in FIG. 3 to the circumference of arc 3 divided by the ratio of the opening width of the openings, $WO_4$, in FIG. 4, to the circumference of the measuring arc $A_4$ or given in formula form:

$$RV = (WO_3/CA_3)/(WO_4/CA_4)$$

where RV is the ratio of angular velocities of shields 92 and 90, $WO_4$ is the width of an opening as measured along measuring arc $A_4$ in shield 90, $CA_4$ is the circumference of measuring arc $A_4$, $WO_3$ is the width of the opening in shield 92 as measured along arc $A_3$ and $CA_3$ is the circumference of measuring arc $A_3$. As previously discussed, the measuring arcs $A_3$ and $A_4$ are proportionally the same distance from the centers of gravity 38 of the shields but are not necessarily and in fact, usually are not precisely the same distance from centers of gravity 38. The distances of $A_3$ and $A_4$ from centers of gravity 38 are proportionally the same when they cross the intersected radiation pyramid sections at proportionally the same locations. The most desired shield shape is circular due to the fact that it is rotated; however, other shield shapes can be used.

When varying shield angular velocities are used, in order to optimize the amount of radiation passing from the shield closest to the source through the remaining shields, it is desirable that the angular velocity and the number of openings in shields be related by the following formula:

$$NP = X$$

where N is the number of intersected flux pyramid sections which will fit around the shield ($360°/\theta_F = N$) where $\theta_F$ is the angle of the widest arc of the flux pyramid; X is the width of the openings + adjacent solid shield areas divided by opening width; and P equals the fractional increase in angular velocity.

In operation, motor 82 drives motor sprocket 76 and by means of chain 78, in turn drives sprocket 74 which turns drive shaft 58. Sprocket 64 attached to drive shaft 58 in turn moves chain 62 and additional shield sprocket 60. Shield sprocket 60 then turns shaft 37 which is attached to and rotates additional shield 34. Sprockets 56 and 57 are similarly rotated by drive shaft 58 and move chains 54 and 55 which rotate sprockets 52 and 53. Sprockets 52 and 53 are attached to and turn shafts 35 and 36 respectively which rotate shields 32 and 31. As shown in FIG. 1, shields 31, 32 and 34 rotate at the same angular velocity and openings 84 are aligned in proportionally the same locations within their respective intersected pyramid sections 86. Radiation passes from source 10 toward detector 16; however, shield 34 intersects and stops all radiation except radiation which passes through openings 84 in shield 34. Radiation passing through openings 84 in shield 34 passes through object, ie., patient 20 and through aligned holes 84 in shields 31 and 32 to detector 16.

As the shields rotate, openings 84 in all of the shields move in such a way that radiation actually scans through patient 20. Radiation passing from a uniform source though openings 84 when shields 31, 32 and 34 are rotated, would scan utilized detector surface 14 in a uniform manner, not considering unequal distances from various positions in the detector to the source.

Radiation which passes through openings 84 in shield 34 and is scattered within patient 20 is usually absorbed by shields 31 and 32 since after scattering it is generally no longer properly aligned with holes 84 in shields 30. Shield 34, as previously mentioned, absorbs all radiation except radiation which passes through openings 84 in alignment with appropriate openings in shields 31 and 32. Patient 20 is therefore not being unnecessarily exposed to radiation which would normally be intercepted by the solid shield areas 88 of shields 84. Shields 31 and 32 as previously mentioned, absorb scattered radiation, therefore, radiation which is actually detected by utilized surface 14 of detector 16 has much sharper contrast since the background of any image detected by detector 16 has very low contamination from scattered radiation.

Due to the much higher contrast obtainable through the utilization of the apparatus and process of the invention, it is possible to use lower radiation dosages to obtain acceptable images or else when radiation dosages are used, which are comparable to those utilized in the prior art, substantially superior images are obtained with the process and apparatus of the invention.

It is to be understood that any suitable means for rotatably mounting the shields in a spatially separated relationship with each other can be used without departing from the spirit of the invention and any suitable means for rotating each of the shields at its own appropriate angular velocity to obtain a constant angular velocity ratio can be used, such as stepping motors, chains and sprockets, positive drive belts or gears.

The openings through the shields can be any desirable shape provided that they are selected to appropriately align with openings in the remaining shields and provided that as previously discussed, the ratio (R) of the sum of the widths of the openings to the sum of the widths of solid shield areas is the same around any circle passing through the flux pyramid having its center at the center of gravity. Although it is not necessary, in general, both the front shield surface 44 facing the radiation source and the rear shield surface 45 facing the detector are planar and are relatively large compared with the thickness 47 of the radiation shields. The shafts 35, 36 and 37 which rotate the shields, generally each lie along its own axis 49 which passes through the center of gravity 38 of its shield and is most desirably perpendicular to the plane of the section of the flux pyramid intersected by the shield. The centers of the shields lie on a single straight line 101 which passes through the centers of the shields to the source. Line 101 is generally outside of the flux pyramid. Axes 49 all intersect with but are not the same as line 101. The shields are most desirably in planes parallel to the plane of the detector.

Figure 2:
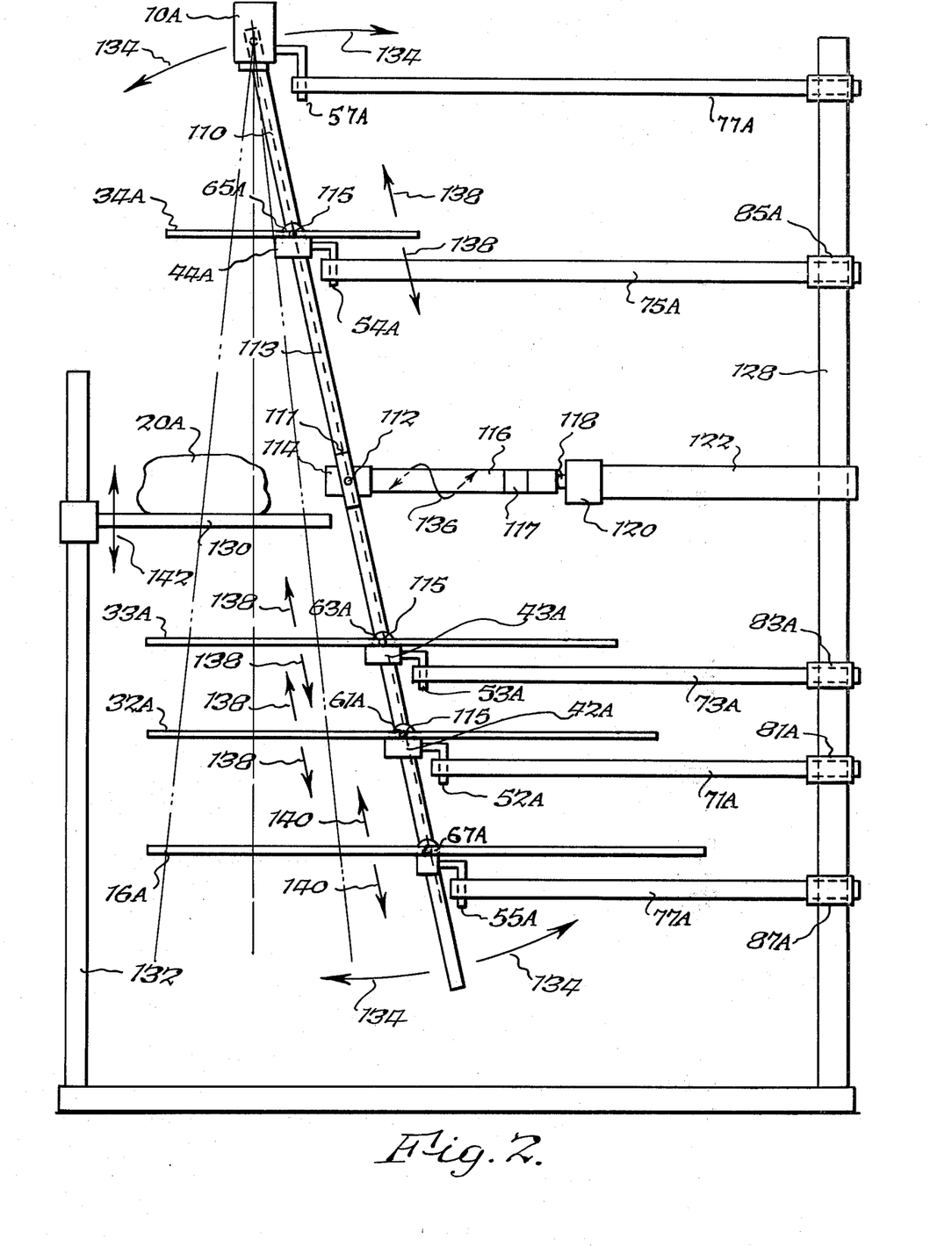
FIG. 2 is a side schematic view of an alternative embodiment of the apparatus as contemplated in accordance with the invention.

In an alternative embodiment of the process of the invention, the source, object, rotatable shields and detector are all moved in relationship to each other while the radiation source is active and while the object, detector and shields all continue to intersect the flux pyramid, continue to remain in planes parallel to the plane of their initial position and while constant proportional distances are maintained. "Constant proportional distances" means that the relationship of the distances between the source, object, shields and detector (collectively called components) to constant points on the components remains constant even though such distances may be increased or decreased by movement of the components. That is, if any one distance between two components increase the distances between the remaining components increase proportionally the same amount and if any one distance between components decreases, the distances between remaining components decreases by proportionally the same amount. In accordance with an apparatus of an alternative embodiment, means is provided for changing the relationship of the source, object, detector and shields to each other from initial positions even while the radiation source is active and while the object, detector and shields all continue to intersect the flux pyramid, continue to remain in planes parallel to the plane of their initial position and while constant proportional distances are maintained. In other respects, the process and apparatus is as previously described. FIG. 2 shows an alternative embodiment of the invention as previously described.

Referring to FIG. 2, the shields 32A, 33A and optionally additional shield 34A are each provided with their own synchronous drives, which may be stepping motors 42A, 43A and 44A respectively. Source 10A, is secured to rotatable arm 110 which is pivotally mounted on bearing 112 to automatic cam drive 114. Arm 110 is provided with a U shaped portion 111 which permits bearing 112 to be located on a line 113 which passes through the centers 115 of shields 32A, 33A and 34A. Motors 42A, 43A and 44A and detector 16A are pivotally secured to arm 110 by means of hinged pivot rods 61A, 63A, 65A and 67A respectively, which rods are behind the shields as viewed in the drawing. Cam drive 114 in turn is secured to rotatable cylinder 116 which is secured by means of cylinder pivot 118 to cylinder cam drive 120. Cylinder 116 is provided with L shaped portion 117 which permits cylinder 116 to rotate about a line passing through bearing 112. Cylinder cam drive 120 is in turn secured to support arm 122 which in turn is mounted to frame 128. An object 20A is placed on table 130 which is secured to frame support 132. Arm 110 can rotate on pivot 112 in the direction shown by arrows 134 and cylinder 116 can rotate on pivot 118 in the directions shown by arrows 136. Motors 42A, 43A and 44A are provided with slide arms 52A, 53A and 54A respectively and detector 16A is provided with slide arm 55A. Slide arms 52A, 53A, 54A and 55A pass through guide openings (not shown) in leveling arms 71A, 73A 75A and 77A respectively. Leveling arms 71A, 73A, 75A and 77A pass through guide openings (not shown) in rotatable guides 81A, 83A, 85A and 87A respectively. Rotatable guides 81A, 83A, 85A and 87A are rotatably mounted to frame upright 128 so that they rotate about the longitudinal axis of upright 128. Source 10A is similarly secured by slide arm 57A and leveling arm 77A.

In operation, the apparatus as shown in the alternative embodiment can be used for conventional tomography or fluoroscopy. For tomography, it is apparent that the source, detector and shields can move relative to object 20A in multiple degrees of motion and is thereby able to blur out all but a selected plane within object 20A which one desires to examine, while shields 32A, 33A and 34A are held in horizontal parallel positions by their respective slide arms and leveling arms. The multiple degrees of motion can be exercised independently or simultaneously to form any desired pattern by selecting appropriate cam motions in drives 114 and 120. Shields 32A, 33A and 34A are secured to shafts of synchronous drives 42A, 43A and 44A and drives 42A, 43A and 44A are secured to arm 110 by means of hinged pivot rods 61A, 63A and 65A respectively and detector 16A is secured to arm 110 by hinged pivot rod 67A.

For changing shield distance, eg., if desired for fluoroscopy, the rods can be loosened so that shields 32A, 33A and 34A and detector 16A can be moved along arm 110 as shown by arrows 138 and 140 and again securely fastened. Motion along arm 110 by shields 32A, 33A and 34A can be accomplished without changing alignment of openings in the shields especially when openings are in the form of circular sectors in the same number at proportionally the same spacing. The object itself can be moved by changing the position of table 130 on frame support 132 as shown by arrows 142.

What is claimed is:

1. An apparatus for reducing detection of radiation scatter from an object through which high energy radiation passes within a flux pyramid from a source to a radiation detection means, said apparatus comprising:
   (a) a series of at least two radiation shields, each of said shields having a front surface and a rear surface, said front and rear surfaces being large relative to the thickness of the shield;
   (b) means for rotatably mounting said shields, in a spatially separated relationship with each other, between the object and the detection means, and so each of said shields covers an entire section of the flux pyramid and is rotatable about its own central axis through its center of gravity, and so the front surface of each shield faces toward said source and the rear surface of each shield faces away from said source;
   (c) means for rotating each of said shields at its own angular velocity at a constant angular velocity ratio; and
   (d) means for changing the relationship of the source, object, detector and shields to each other from initial positions while the object, detector and shields all continue to remain in planes parallel to the planes of the initial positions and continue to intersect the flux pyramid while constant proportional distances are maintained;
each of said shields being provided with a series of openings, smaller than the object, passing through the shield from the front to the rear surface, which openings allow radiation to pass through the shield from the source to the detection means, each of said shields being provided with such openings in shapes and positions such that at least a portion of radiation in a straight line from said source toward said detection means passes through openings in all of said shields to strike the detection means in essentially uniform coverage of said detection means when said object is absent, when the source is uniform and when each of said shields is in rotation about its central axis at its own angular velocity at a constant angular velocity ratio.

2. The apparatus of claim 1 wherein the central axis of each shield is approximately perpendicular to the detector plane.

3. The apparatus of claim 1 wherein the ratio of the sum of the widths of the openings to the sum of the widths of solid shield areas is essentially constant on each shield as such widths are measured along the entire arc of any circle having its center at the central axis of the shield and passing through the flux pyramid.

4. The apparatus of claim 3 wherein the ratio of the sum of the widths of the openings to the sum of the widths of the solid shield areas on each shield is at least as large as such ratio for each such shield which is closer to the source.

5. The apparatus of claim 3 wherein the ratio of any opening to the width of any adjacent solid shield area as measured along any arc of a circle having its center at the central axis and passing through the flux pyramid is constant and is the same as such ratio on all other shields along a proportionally identical arc.

6. The apparatus of claim 3 wherein the angular velocities of the shields are the same.

7. The apparatus of claim 6 wherein the openings through each of the shields are in proportionally the same shapes and are disposed in proportionally the same patterns as in the other shields.

8. The apparatus of claim 1 wherein the high energy radiation is x-ray radiation.

9. The apparatus of claim 8 wherein the detection means is a luminescent screen.

10. The apparatus of claim 1 additionally comprising:
(a) An additional radiation shield having front and rear surfaces,
(b) means for rotatably mounting said additional shield between the source and the object in a spacially separated relationship with the other shields so said shield covers an entire section of the flux pyramid and is rotatable about its own central axis through its center of gravity, so the front surface of said additional shield faces toward said source and the rear surface faces away from said source; and
(c) means for rotating each of said shields at its own angular velocity at a constant angular velocity ratio;

said additional radiation shield being provided with a series of openings passing through the shield from the front to the rear surfaces, which openings allow radiation to pass through the shield from the source to the detection means, such additional shield being provided with such openings in shapes and positions such that at least a portion of radiation in a straight line from said source toward said detector means passes through openings in all of said shields to strike the detection means in essentially uniform coverage of said detection means when said object is absent and when each of said shields is in rotation about its central axis at its own angular velocity at a constant angular velocity ratio.

11. The apparatus of claim 10 wherein the central axis of each shield is approximately perpendicular to the detector plane.

12. The apparatus of claim 10 wherein the ratio of the sum of the widths of the openings to the sum of the widths of solid shield areas is essentially constant on each such shield as such widths are measured along the arc of any circle having its center at the central axis of the shield and passing through the flux pyramid.

13. The apparatus of claim 10 wherein the ratio of the sum of the widths of the openings to the sum of the widths of the solid shield areas on each shield is at least as large as such ratio for each such shield which is closer to the source.

14. The apparatus of claim 12 wherein the ratio of any opening to the width of any adjacent solid shield area as measured along any arc of a circle having its center at the central axis and passing through the flux pyramid is constant and is the same as such ratio on all other shields along a proportionally identical arc.

15. The apparatus of claim 12 wherein the angular velocities of the shields are the same.

16. The apparatus of claim 15 wherein the openings through each of the shields are in proportionally the same shapes and are disposed in proportionally the same patterns as in the other shields.

17. The apparatus of claim 16 wherein the high energy radiation is x-ray radiation.

18. The apparatus of claim 17 wherein the detection means is a luminescent screen.

19. A process for reducing detection of radiation scatter from an object by a radiation detector which receives high energy radiation within a flux pyramid through the object from a radiation source, which process comprises:
(a) interposing a series of at least two spatially separated radiation shields between the object and a utilized surface of the detector, such that each of the shields covers an entire section of the flux pyramid, each of said shields having a front surface and a rear surface, said front and rear surfaces being large relative to the thickness of the shield, the front surface of each shield facing the radiation source, each shield having a central axis passing through its center of gravity in a direction substantially perpendicular to the front surface, each shield being provided with openings smaller than the object passing through said shield from the front to the rear surface, the ratio of the sum of the widths of the openings to the sum of the widths of solid shield areas being constant as such widths are measured along the arc of any circle having its center at the central axis of the shield and passing through the flux pyramid;
(b) aligning said shields so that at least a portion of radiation in a straight line from said source toward said detector within the flux pyramid passes through openings in each of said shields to strike said detector;
(c) rotating each of said shields about its central axis at its own angular velocity at a constant angular velocity ratio to permit at least a portion of radiation in a straight line from said source toward said detector; and
(d) changing the relationship of the source, object, detector and shields to each other from initial positions while the object, detector and shields all continue to remain in planes parallel to the planes of the initial positions and continue to intersect the flux pyramid while constant proportional distances are maintained.

20. The process of claim 19 wherein said shields have parallel planar front and rear surfaces.

21. The process of claim 19 wherein the angular velocities of the shields are the same.

22. The process of claim 21 wherein the openings through each of the shields are in proportionally the same shapes and are disposed in proportionally the same patterns as in the other shields.

23. The process of claim 22 wherein the high energy radiation is x-ray radiation.

24. The process of claim 23 wherein the detector is a luminescent screen.

25. The process of claim 19 wherein said process further comprises interposing an additional radiation shield between the source and the object, such that said additional shield covers an entire section of the flux pyramid, said additional shield also having said front and rear surfaces, said central axis and said openings; aligning said shields so that at least a portion of radiation in a straight line from said source toward said detector within the flux pyramid passes through openings in each of said shields to strike said detector; and rotating each of said shields about its central axis at its own angular velocity at a constant angular velocity ratio to permit at least a portion of radiation in a straight line from said source toward said detector within the flux pyramid to pass through openings in all of the shields to strike the detector in essentially uniform coverage of the utilized detector surface when the object is absent.

26. The process of claim 25 wherein said shields have parallel planar front and rear surfaces.

27. The process of claim 25 wherein the angular velocities of the shields are the same.

28. The process of claim 27 wherein the openings through each of the shields are in proportionally the same shapes and are disposed in proportionally the same patterns as in the other shields.

29. The process of claim 28 wherein the high energy radiation is x-ray radiation.

30. The process of claim 29 wherein the detector is a luminescent screen.

31. The apparatus of claim 1 wherein means is provided for moving said shields closer to or further from said source while retaining the location of their centers on the same line passing from the source.

32. The apparatus of claim 10 wherein means is provided for moving said shields closer to or further from said source while retaining the location of their centers on the same line passing from the source.

33. The apparatus of claim 13 wherein means is provided for moving said shields closer to or further from said source while retaining the location of their centers on the same line passing from the source.

34. The apparatus of claim 14 wherein means is provided for moving said shields closer to or further from said source while retaining the location of their centers on the same line passing from the source.

35. The apparatus of claim 15 wherein means is provided for moving said shield closer to or further from said source while retaining the location of their centers on the same line passing from the source.

36. The apparatus of claim 16 wherein means is provided for moving said shields closer to or further from said source while retaining the location of their centers on the same line passing from the source.

* * * * *